United States Patent
Rachmaninoff et al.

(10) Patent No.: US 12,115,409 B2
(45) Date of Patent: Oct. 15, 2024

(54) STRETCHING DEVICE AND METHODS RELATING TO SAME

(71) Applicants: Vanessa Rachmaninoff, Nashville, TN (US); James Ronald Lawson, Jr., Franklin, TN (US)

(72) Inventors: Vanessa Rachmaninoff, Nashville, TN (US); James Ronald Lawson, Jr., Franklin, TN (US)

( * ) Notice: Subject to any disclaimer, the term of this patent is extended or adjusted under 35 U.S.C. 154(b) by 762 days.

(21) Appl. No.: 16/592,342

(22) Filed: Oct. 3, 2019

(65) Prior Publication Data
US 2021/0101044 A1   Apr. 8, 2021

(51) Int. Cl.
*A63B 21/28* (2006.01)
*A61B 5/00* (2006.01)
(Continued)

(52) U.S. Cl.
CPC ............ *A63B 21/28* (2013.01); *A61B 5/1107* (2013.01); *A61B 5/224* (2013.01); *A61B 5/6807* (2013.01); *A61H 1/02* (2013.01); *A63B 21/0414* (2013.01); *A63B 21/0552* (2013.01); *A63B 21/4015* (2015.10); *A63B 21/4035* (2015.10); *A61B 5/0004* (2013.01); *A61B 5/6828* (2013.01); *A61B 2503/40* (2013.01); *A61B 2560/0475* (2013.01); *A61B 2562/0219* (2013.01); *A61B 2562/0252* (2013.01); *A61B 2562/0261* (2013.01); *A63B 2208/14* (2013.01);
(Continued)

(58) Field of Classification Search
CPC . A63B 21/28; A63B 21/4015; A63B 21/4035; A63B 21/0414; A63B 21/0552; A63B 2208/14; A63B 2209/00; A63B 2220/40; A63B 2220/51; A63B 2220/803; A63B 2225/09; A63B 2225/52; A61B 5/1107; A61B 5/224; A61B 5/6807; A61B 5/0004; A61B 5/6828; A61B 2503/40; A61B 2560/0475; A61B 2562/0219; A61B 2562/0252; A61B 2562/0261; A61H 1/02
See application file for complete search history.

(56) References Cited

U.S. PATENT DOCUMENTS 216,705 A   6/1879   Smith
730,360 A   6/1903   Forsyth
(Continued)

FOREIGN PATENT DOCUMENTS

CA   2909127 A1   9/2014
CN   203506917 U   4/2014
(Continued)

OTHER PUBLICATIONS

Machine Translation of KR 100894914, Patent Translate, 6 pages, printed on Sep. 12, 2022 (Year: 2011).*
(Continued)

*Primary Examiner* — Yi-Shan Yang
*Assistant Examiner* — Om Patel (57) ABSTRACT

A stretching device comprising an elongated band having a first end and a second end, a first handle coupled to the band proximate the first end, a second handle coupled to the band proximate the second end, and a boot coupled to the band between the first end and the second end, the boot adapted to engage with a body part of a person, horse, or other animal.

9 Claims, 6 Drawing Sheets

(51) Int. Cl.
- *A61B 5/11* (2006.01)
- *A61B 5/22* (2006.01)
- *A61H 1/02* (2006.01)
- *A63B 21/00* (2006.01)
- *A63B 21/04* (2006.01)
- *A63B 21/055* (2006.01)

(52) U.S. Cl.
CPC ....... *A63B 2209/00* (2013.01); *A63B 2220/40* (2013.01); *A63B 2220/51* (2013.01); *A63B 2220/803* (2013.01); *A63B 2225/09* (2013.01); *A63B 2225/52* (2013.01)

(56) References Cited

U.S. PATENT DOCUMENTS

| | | | |
|---|---|---|---|
| 3,405,506 | A | 10/1968 | Kostur |
| RE32,547 | E | 11/1987 | Reed |
| 5,277,683 | A * | 1/1994 | Wilkins ............ A63B 21/4015 482/121 |
| 5,782,727 | A * | 7/1998 | Pierce ................ A63B 21/0552 482/121 |
| 5,974,342 | A | 10/1999 | Petrofsky |
| 7,204,041 | B1 | 4/2007 | Bailey, Sr. et al. |
| 2010/0069202 | A1 | 3/2010 | Olsen |
| 2011/0185979 | A1 | 8/2011 | Dunagan |
| 2011/0251033 | A1 | 10/2011 | Blancher |
| 2012/0129653 | A1 | 5/2012 | Shalev et al. |
| 2012/0245002 | A1 | 9/2012 | Todd et al. |
| 2013/0035614 | A1 | 2/2013 | Casha |
| 2013/0203567 | A1 * | 8/2013 | Thomas ........... A63B 21/00043 482/124 |
| 2014/0073496 | A1 | 3/2014 | Bannerman |
| 2014/0274613 | A1 * | 9/2014 | DeMarco ........... A63B 21/4035 29/428 |
| 2014/0373793 | A1 | 12/2014 | McDermott |
| 2016/0296787 | A1 * | 10/2016 | Kamins ............. A63B 21/4013 |
| 2019/0087651 | A1 | 3/2019 | Bose et al. |
| 2019/0269967 | A1 * | 9/2019 | Thomas ........... A63B 21/00185 |

FOREIGN PATENT DOCUMENTS

| | | |
|---|---|---|
| CN | 207605130 U | 7/2018 |
| DE | 3820694 A1 | 12/1989 |
| DE | 10121808 C1 | 7/2002 |
| DE | 10200003 A1 | 1/2004 |
| DE | 102004034366 A1 | 2/2006 |
| DE | 102006051407 B4 | 10/2008 |
| DE | 202010012268 U1 | 3/2011 |
| DE | 102012100183 B4 | 3/2015 |
| FI | 122551 B | 3/2012 |
| KR | 100894914 * | 4/2009 |
| KR | 20110061845 * | 10/2011 |
| WO | WO-9734661 A1 * | 9/1997 ......... A63B 21/0004 |
| WO | WO-2012052769 A1 * | 4/2012 ....... A63B 21/00043 |
| WO | 2017185112 A1 | 11/2017 |
| WO | 2018203172 A1 | 11/2018 |

OTHER PUBLICATIONS

Machine Translation of KR 20110061845, Patent Translate, 7 pages, printed on Sep. 12, 2022 (Year: 2009).*

Notification of International Search Report and Written Opinion issued in corresponding International Application No. PCT/US20/49406, mailed Jan. 29, 2021, 19 pages.

"Elastic Neck Stretcher," listed for sale Online by Waldhausen, 3 pages. Publicly available before the filing date of Oct. 3, 2019, 3 pages. Retrieved from Internet: <https://www.waldhausen.com/en/horses/training-equipment/elastic-neck-stretcher.html#more>.

Unknown, "Stretching Lungeing Workout Session with Sliding Side-Reins", Horse Pilates, electronically published Jan. 30, 2015, 4 pages. Retrieved from Internet: <http://lungeing-training.com/stretching-lungeing-workout-session-with-sliding-side-reins/>.

Screen captures from YouTube video clip entitled "Pessoa Training System with Molly Rosin", 4 pages, uploaded on May 22, 2012, by user "Bit of Britain". Retrieved from Internet: <https://www.youtube.com/watch?v=V23UV6E_dhc>.

Screen captures from YouTube video clip entitled "How to lunge a horse with a Chambon lunge device", 5 pages, uploaded on Dec. 7, 2009, by user "Horsemart". Retrieved from Internet: <https://www.youtube.com/watch?v=3zokDbRn73s>.

Screen captures from YouTube video clip entitled "Arioneo Orscana Horse Health Monitor", 6 pages, uploaded on Feb. 16, 2017, by user "Urban Horses", Retrieved from Internet: <https://www.youtube.com/watch?v=ebu7FH0kP9g>.

Screen captures and audio transcription from YouTube video clip entitled "HHP MassageBlanket English", 5 pages, uploaded on Jul. 5, 2012, by user "InFamous Productions", Retrieved from Internet: <https://www.youtube.com/watch?v=pLwTUL-PrGo>.

Unknown, "Steed—the world's first halter-free biometric wearable device for horses", Steed, publicly available before the filing date of Oct. 3, 2019, 4 pages. Retrieved from Internet :<http://www.steedwatch.com/>.

Nguyen, My, "Wearable Health Trackers for Horses", Wearable-Technologies, published electronically on Apr. 6, 2016, 1 page. Retrieved from Internet: <https://www.wearable-technologies.com/2016/04/wearable-health-trackers-for-horses/>.

Unknown, "Case Study: How Eliza gets peace of mind with Trackener", Trackener, publicly available before the filing date of Oct. 3, 2019; 3 pages. Retrieved from Internet: <https://www.trackener.com/en/product>.

* cited by examiner

STRETCHING DEVICE AND METHODS RELATING TO SAME

TECHNICAL FIELD

This invention relates to a device to aid in stretching people, horses, and other animals and methods relating to same.

BACKGROUND

Stretching is done in order to prevent, diagnose, and rehabilitate soft tissue injuries in both people and animals. In some instances, a person, such as a medical practitioner or trainer, will aid a subject (a person or an animal) in stretching by applying tension or pressure to the subject in order to stretch specific muscles or muscle groups.

One problem encountered when stretching subjects is the lack of precision. The practitioner or trainer does not measure the amount of force applied to the subject or the amount of stretching achieved, and instead subjectively judges those amounts based on their personal experience. Accordingly, it is difficult to compare the flexibility of different subjects, especially when the subjects are treated by different practitioners.

A further problem is encountered when the subject is a large animal, such as a horse. A practitioner may be required to exert a large amount of force when performing some stretches on a large subject. This force may need to be applied with the practitioner in an awkward or uncomfortable position, risking injury to both the practitioner and the subject. For example, an equine practitioner may need to bend over to lift individual legs of a horse. Both the weight of the horse's legs as well as the strength of the horse if it moves pose risks to the practitioner.

Therefore, a need exists for a device to improve stretching and to aid in diagnosing and treating injuries.

SUMMARY OF THE INVENTION

An exemplary stretching device has an elongated configuration with a handle on each end. The device includes a band positioned between the two handles. A padded portion, or boot, is attached to the band. In one embodiment, the band extends around the exterior of the boot. In another embodiment, the band has separate right and left portions, each attached to a respective side of the boot.

In some embodiments, the boot is detachably coupled to the band, such as by hook and loop fasteners, adhesive, buckles, snaps, or other means. The boot is adapted to engage with the leg (or other part of a subject) such that pulling on the handles of the band exerts force on the subject's leg through the boot. The boot can be detached from the band and another boot adapted to engage a specific part of the subject can be attached to the band. The boot may have a cushioned portion on its interior surface for engaging the subject.

In some embodiments, the stretching device includes at least one sensor for sensing the amount of force applied to the subject through the boot and the band by pulling on the handles. Alternatively or additionally, the stretching device includes at least one sensor for sensing the orientation and movement of the portion of the subject being stretched.

In use, the band is at least partially wrapped around a subject person, horse, or other animal with the boot resting against the subject. The user grips the device by the handles and pulls on the device in order to apply a stretching force to the subject.

The stretching device is useful in diagnosing, treating, and rehabilitating orthopedic and other types of injuries in people, for example, sports injuries, and in horses and other animals. Thus, the stretching device is useful to both medical practitioners, physical therapists, veterinarians, and trainers.

Elements in the figures are illustrated schematically for simplicity and clarity and have not necessarily been drawn to scale or to include all features, options or attachments. For example, the dimensions and/or relative positioning of some of the elements in the figures may be exaggerated relative to other elements to improve understanding of various embodiments of the present invention. Also, common, well-understood elements that are useful or necessary in a commercially feasible embodiment are often not depicted in order to facilitate a less obstructed view of various embodiments of the present invention. Certain actions and/or steps may be described or depicted in a particular order of occurrence while those skilled in the art will understand that such specificity with respect to sequence is not actually required. The terms and expressions used herein have the ordinary technical meaning accorded to such terms and expressions by persons skilled in the technical field as set forth above except where different specific meanings have otherwise been expressly set forth herein.

DETAILED DESCRIPTION

Figure 1A:
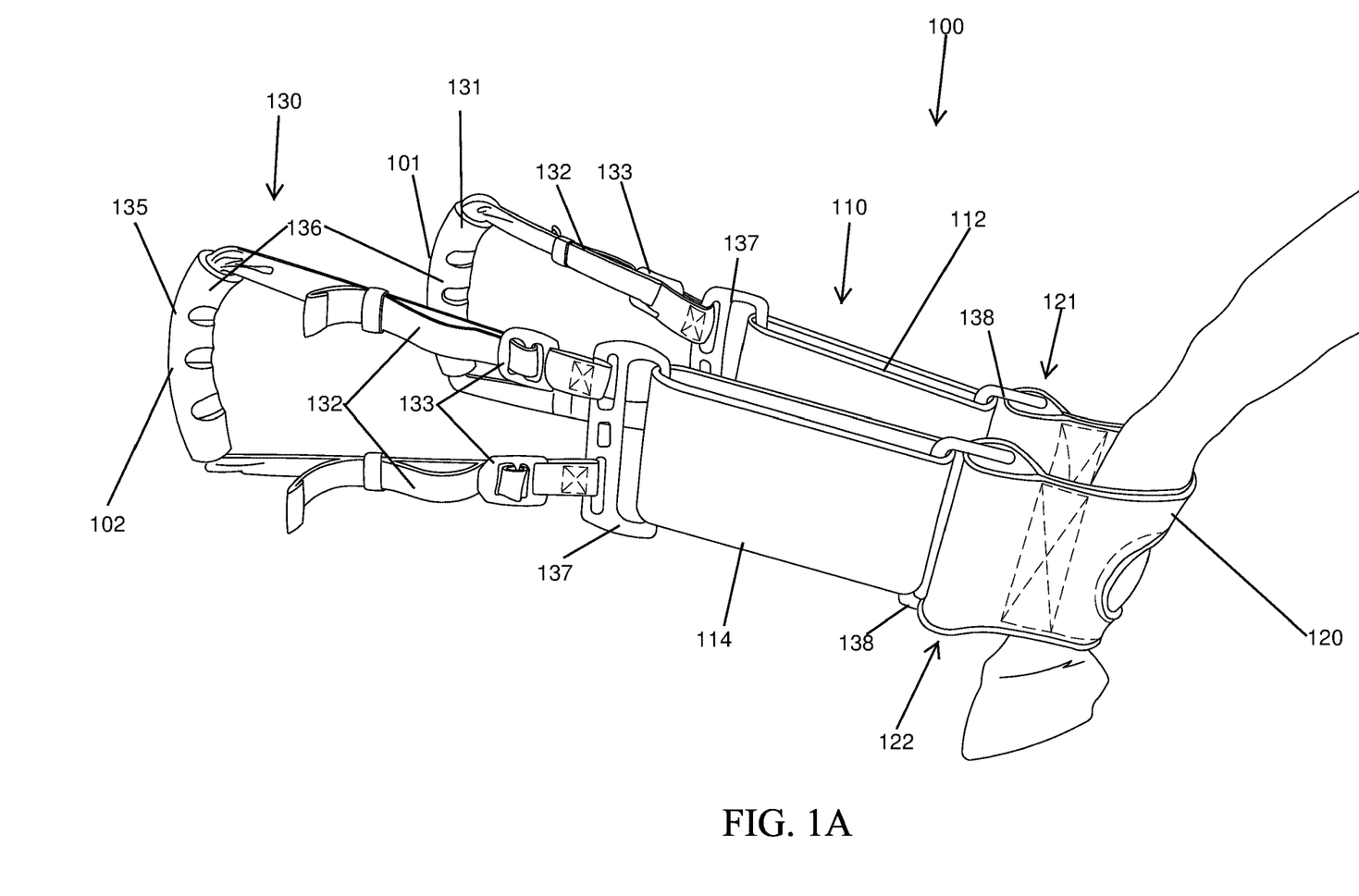
FIG. 1A is a perspective view of a stretching device in accordance with embodiments of the present invention.
Figure 1B:
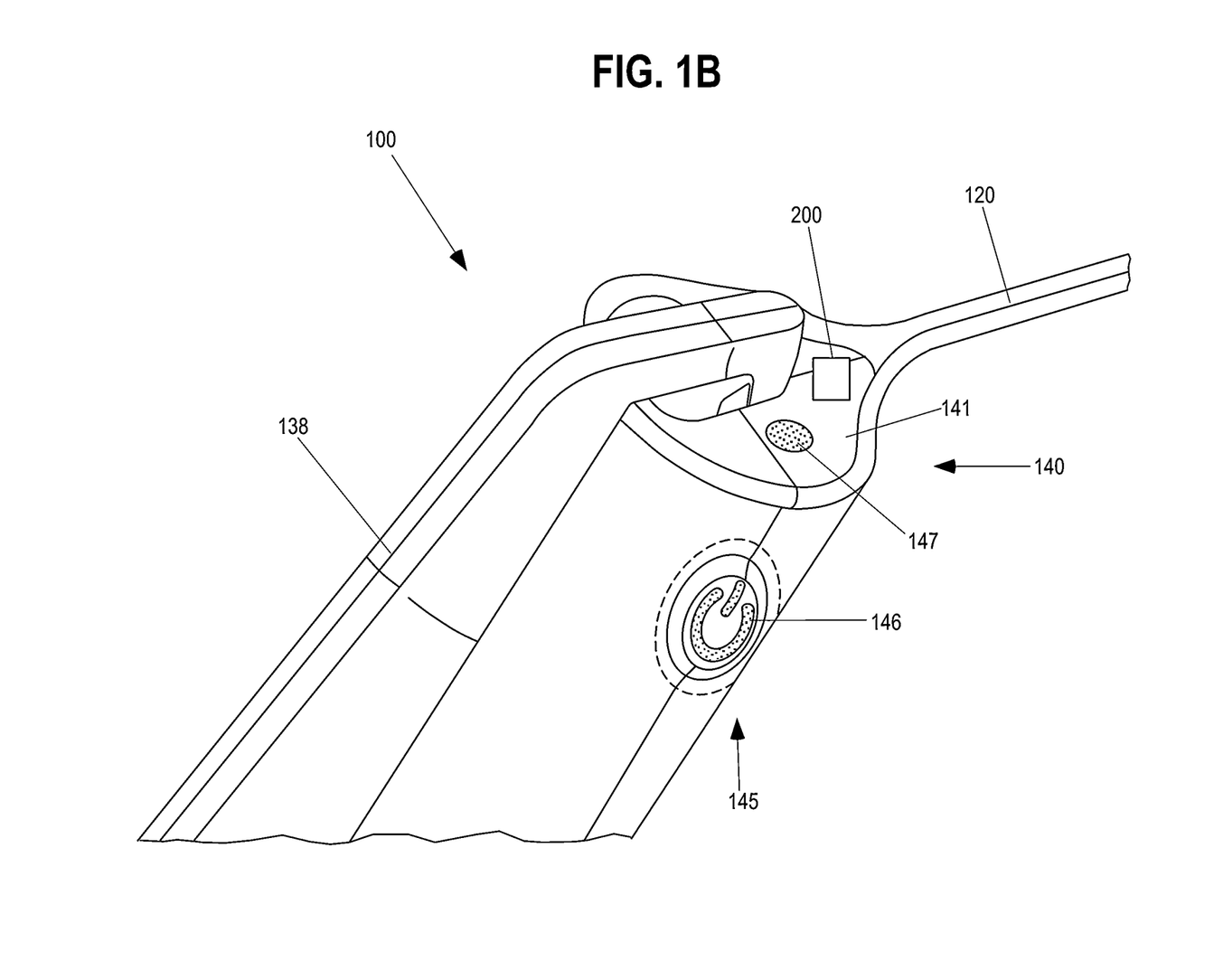
FIG. 1B is an expanded view of a portion of the stretching device of FIG. 1A illustrating a sensor of the device.

FIGS. 1A-1B illustrate a stretching device 100. The stretching device 100 has an elongated body having a first end 101 and a second end 102. The stretching device 100 includes a band 110, a boot 120, and pair of primary handles 130. The band 110 includes a first section 112 and a second section 114. The two band sections 112/114 are resilient or elastic. The band sections 112/114 are elastic because they are formed of an elastic material, include one or more springs, and/or include resilient folds. In operation, the elasticity of the band 110 dampens movement of the subject's body by the user. This dampening reduces the risk of injury to the subject or the user by a sudden exertion of force upon the subject's body.

The boot 120 is detachably coupled to the band 110. In some forms, the boot 120 includes two ends 121/122 which are coupled to respective band sections 112/114 as shown. In alternative forms, the band 110 continues along the length of the boot 120 and the boot 120 is coupled to a face of the band 110.

In a preferred form, the boot 120 is at least partially formed of a deformable material in order to more comfortably conform to the shape of the subject's body part being stretched. For example, the boot 120 is formed of a rubber material (such as neoprene) or a foam material. In some forms, the boot 120 is shaped to conform to a specific body part, such as a leg. Different boots 120 are provided having different shapes adapted for stretching different body parts.

The handles 130 are coupled to respective ends of the band 110 such that the first handle 131 is located proximate the first end 101 of the stretching device 100, and the second handle 135 is located proximate the second end 102 of the stretching device 100. In a preferred form, the handles 130 are at least partially formed of a deformable material, such as rubber or foam, to provide a more comfortable grip for the user. Alternatively or additionally, the handles 130 are ergonomically shaped. The comfortable grip aids the user in exerting relatively large forces on the subject during stretching, for example when stretching a large animal. Additionally, the use of deformable and/or ergonomic grips 136 on the handles 130 reduces the risk of the user's grip slipping, which may cause injury to the user and/or the subject.

The stretching device 100 has an adjustable length such that the device can be customized for specific users, subjects, and stretches. The handles 130 include straps 132 and fasteners 133 between the grips 136 and the band 110 to enable the length of the handles 130 to be adjusted. Additionally, the handles 130 are detachably coupled to the band 110. The stretching device 100 includes second additional handles 137 located between the primary handles 130 and the band 110. When the primary handles 130 are removed, the user can use the stretching device 100 by gripping the additional handles 137. Similarly, the stretching device includes additional handles 138 located between the band sections 112/114 and the boot 120. In use, the band sections 112/114 can be removed and the stretching device 100 can be used by gripping the handles 138.

In some embodiments, the stretching device 100 includes a sensor assembly 140. As shown schematically in FIG. 1B, the sensor assembly 140 includes a sensor housing 141 containing a sensor circuit 200. In some forms, the sensor assembly 140 further includes a user interface 145. The user interface 145 includes one or more user inputs 146, such as a power button. In one form, the user interface 145 includes outputs, such as a display configured to display readings from the sensors or an audible output. Alternatively or additionally, the sensor circuit includes a wireless transmitter for transmitting sensor data to a computing device, such as a smart phone, tablet, or other computing device. The user then views the data on the computing device. The user interface 145 includes an input for establishing a wireless connection between the sensor circuit 200 and the computing device 220, such as a button 147 for putting a Bluetooth transceiver of the sensor circuit 200 into a pairing state.

Figure 2:
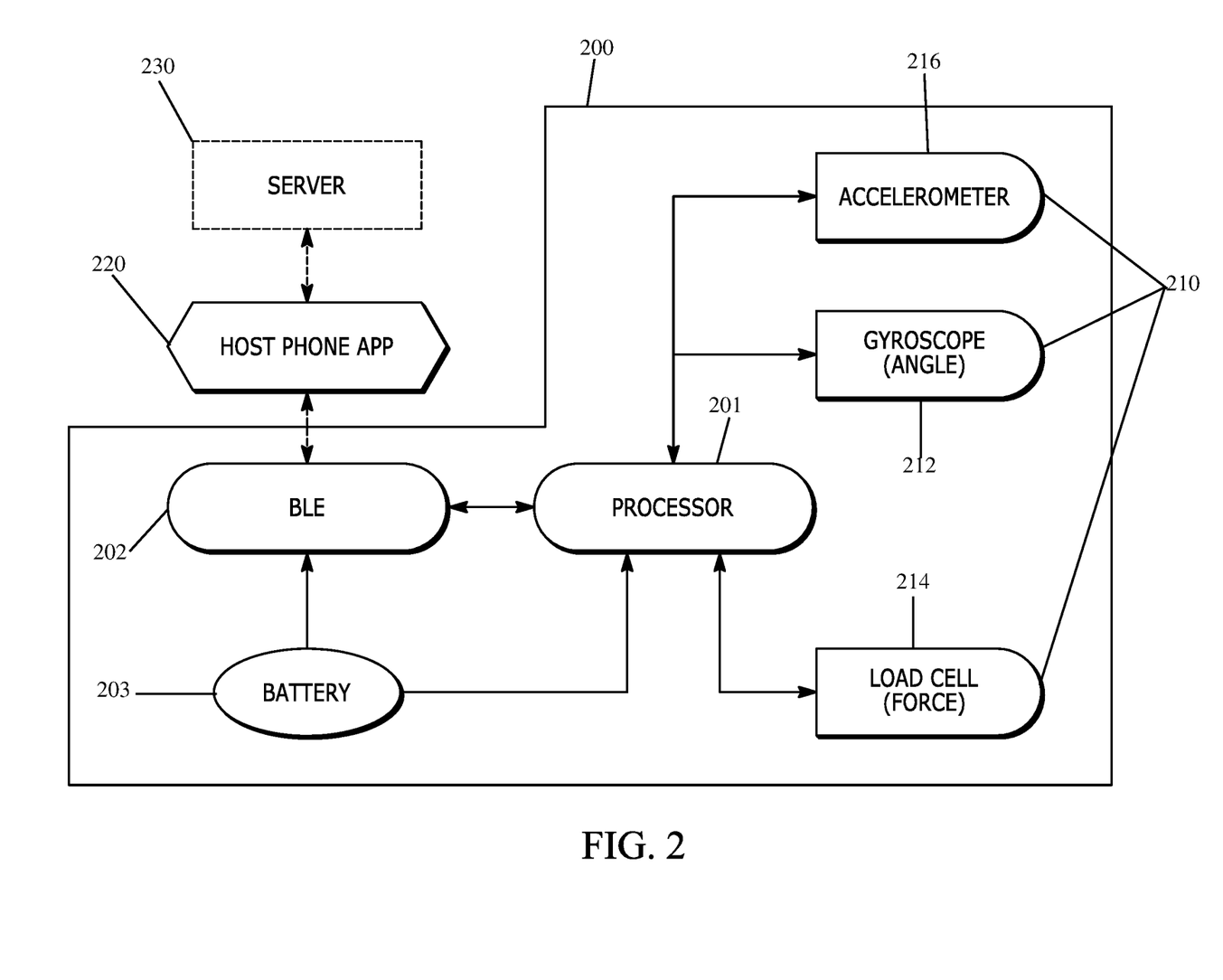
FIG. 2 is a block diagram illustrating the sensor circuit of a stretching device in accordance with embodiments of the present invention.

FIG. 2 illustrates the sensor circuit 200. The sensor circuit 200 includes a processor 201 operatively coupled to the sensors 210. The sensors 210 monitor one or more of the orientation, direction, and amount of movement of the subject's body part during stretching. The sensors 210 include, among other things, an orientation sensor 212, such as a gyroscope or mercury switch. The sensors 210 further include a force sensor 214, such as a strain gauge or load cell configured to directly or indirectly sense the amount of force imparted on the subject by the stretching device 100. Alternatively or additionally, the sensors 210 further include a movement sensor 216, such as an accelerometer, configured to sense direction and acceleration when the stretching device 100 is moved to provide data enabling the device to track the direction and amount of movement of the boot during stretching. The accelerometer 216 also provides orientation information (relative to the starting position). The amount of movement indicates the full range of motion of the subject's body part during stretching. In some forms, the accelerometer 216 is used to determine orientation by tracking movement over time. The sensors 212 and 216 are used to detect the force imparted on the subject. For example, a sensor used to measure distance can be used to measure the deformation of the stretching device, such as the amount the band stretches or the amount the boot compresses. Deformation of portions of the stretching device can be measured by strain gauges or load cells in order to measure the amount of force being applied to the subject, such as the amount of force being used to stretch the leg of a horse.

In operation, the processor 201 receives data from the sensors 210 representing the measured values. It is understood that the sensor circuit 200 may include additional sensors. For example, the sensor circuit 200 may include sensors for monitoring the conditions, such as temperature sensors. Alternatively or additionally, the sensor circuit 200 may include other sensors for monitoring the subject, such as a heart rate or blood pressure sensor.

The sensor circuit 200 further includes a wireless communication device 202, such as a wireless transmitter, transceiver, and/or receiver. The wireless communication device 202 transmits data from the processor 201 to a computing device 220, such as a smart phone or computer. The wireless communication device 202 communicates over a known communication protocol, such as Bluetooth®, BLE, WiFi, infrared, Zigbee, etc. In some forms, the wireless communication device 202 receives data from the remote computing device 220 in order to control the sensor circuit 200. As discussed above, in some forms, the sensor circuit 200 includes a display or other user interface for directly communicating data to a user.

A power supply 203, such as a battery, powers the sensor circuit 200. In some forms, the power supply 203 includes a rechargeable battery and a charging means, such as a charging cable port or an induction coil for wireless charging. In alternative forms, the power supply 203 includes a power cable or a removable battery.

In operation, the processor 201 receives data from the sensors 210 and transmits the data, via the wireless communication device 202, to the computing device 220. In some forms, the processor 201 performs operations on data received from the sensors 210 and transmits the results of such operations to the computing device 220. The computing device 220 uses a processor running software, such as an app, to process the data and display or otherwise communicate the data to the user. In one form, the app parses the data received from the processor 201 for maximum or minimum values and displays those values to the user. For example, the app displays the greatest range of motion achieved by the stretch and the maximum amount of force applied to the body part by the boot during the stretch. Alternatively or additionally, the app displays smoothed or averaged values, such as the average amount of force applied during the stretching period.

In some forms, either the app, the sensor circuit 200, or both provide outputs to the user during stretching. For example, the app or the sensor circuit 200 includes a timer for timing individual stretches and outputs an audible alert when the desired time has elapsed. In other forms, the app or the sensor circuit 200 outputs an alert when a predetermined limit, such as a maximum distance of stretching or a maximum amount of force applied, is reached.

The computing device 220 includes memory (not shown) for storing sensor data received from the processor 201 and data pertaining to the subject in addition to an app. In one form, the computing device 220 correlates the stored sensor data with subject data. Subject data includes data identifying the specific subject, such as by name or other unique identifier, as well as data describing the subject, such as species/breed, age, activity level, prior stretching sessions, and injury status.

In some embodiments, the external computing device 220 is communicatively coupled to a server 230. The server 230 receives sensor data and corresponding subject data from, among other sources, a plurality of stretching devices 100. The server 230 includes a processor running software for identifying trends, for example, maximums, minimums, and averages in sensor data based on the subject data. In some forms, the server 230 transmits data to the computing device 220 for comparison to the measured data for an individual subject. For example, if the subject is a horse, the server 230 transmits average or expected measurements based on stored sensor values from horses of the same or similar breed, size, age, injury status, and activity level/type. This enables the user to identify potential injury concerns in the subject.

In some forms, the compiled data in the server 230 is also used to recognize trends to avoid potential injuries. For example, the server 230 software could identify an increase in stiffness or injury among race horses after running on a specific track or under specific weather or track conditions. Similarly, the server 230 software is usable to identify trends specific to certain activity types, for example trends among harness racing horses, in order to prevent potential injuries.

Figure 3A:
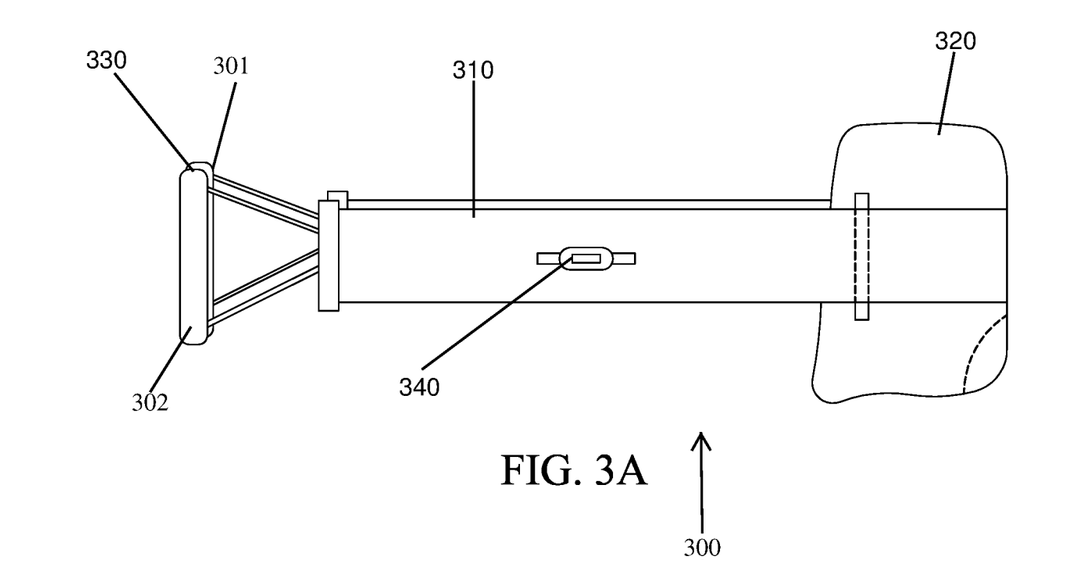
FIG. 3A is a side elevational view of a stretching device in accordance with embodiments of the present invention.
Figure 3B:
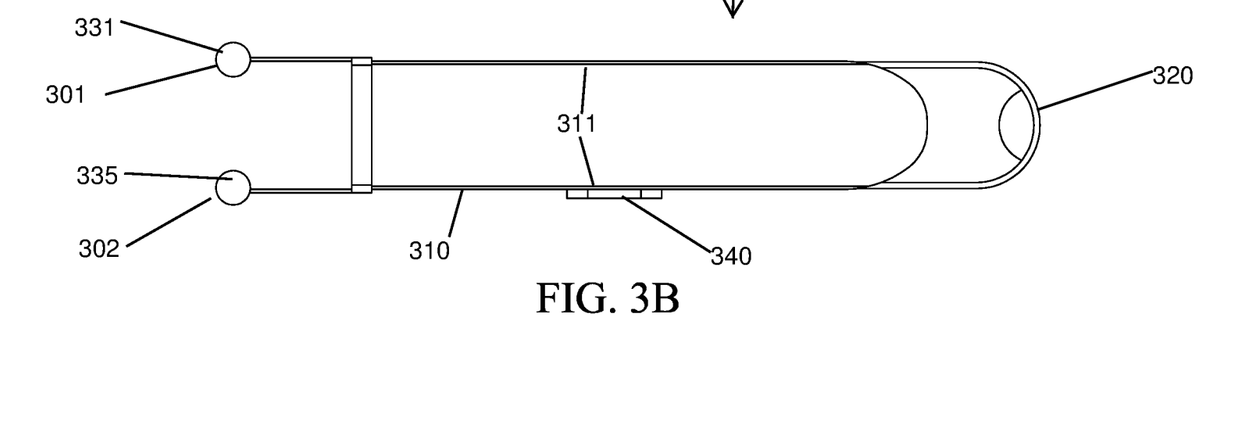
FIG. 3B is a top view of the stretching device of FIG. 3A.

FIGS. 3A-3B illustrate a stretching device 300 according to another embodiment of the present invention. In use, the stretching device 300 is used similarly to the stretching device 100. The stretching device 300 has an elongated shape with a first end 301 and a second end 302. The stretching device 300 includes a pair of handles 330 positioned proximate respective ends with a first handle 331 at the first end 301 and a second handle 335 at the second end 302 of the device. A band 310 extends between the two handles 330. A boot 320 is mounted to an internal surface 311 of the band 310.

The band 320 is formed of an elastic material. In operation, the band 320 extends when force is applied to the handles 330 and/or the boot 320. The band 320 contracts when the force on the handles 330 and/or the boot 320 is reduced. By expanding and contracting, the band 320 reduces the transfer of sudden changes in force on the handles 330 or the boot 320 to the other of the handles 330 or the boot 320. This reduces the risk of injury to the user or the subject as the result of a sudden movement by the other of the user or the subject.

A sensor device 340 is mounted on the band 310. The sensor device 340 includes a sensor configured to measure the distance between two points on the band 310. As applied forces cause the band 310 to expand and contract, the distance between the two points changes. From the change in distance and the known spring constant of the band 310, the sensor device 340, such as a strain gauge, measures the amount of force imparted on the subject by the user. Alternatively or additionally, the sensor device 340 includes a load cell to measure the force applied between the handles 330 and the boot 320.

In some forms, the sensor device 340 further includes a wireless communication device. The wireless communication device transmits the measured sensor data from the sensor device 340 to a computing device, such as a smart phone. The smart phone processes, displays, outputs, and/or transmits the data to a server as described in previous embodiments.

As discussed above, the boot 320 preferably is made of a deformable material, such as neoprene, to more comfortably engage the subject. The boot 320 is detachably coupled to the band 310. In some embodiments, a plurality of different shaped boots 320 are provided for use when stretching different parts of the subject.

Figure 4A:
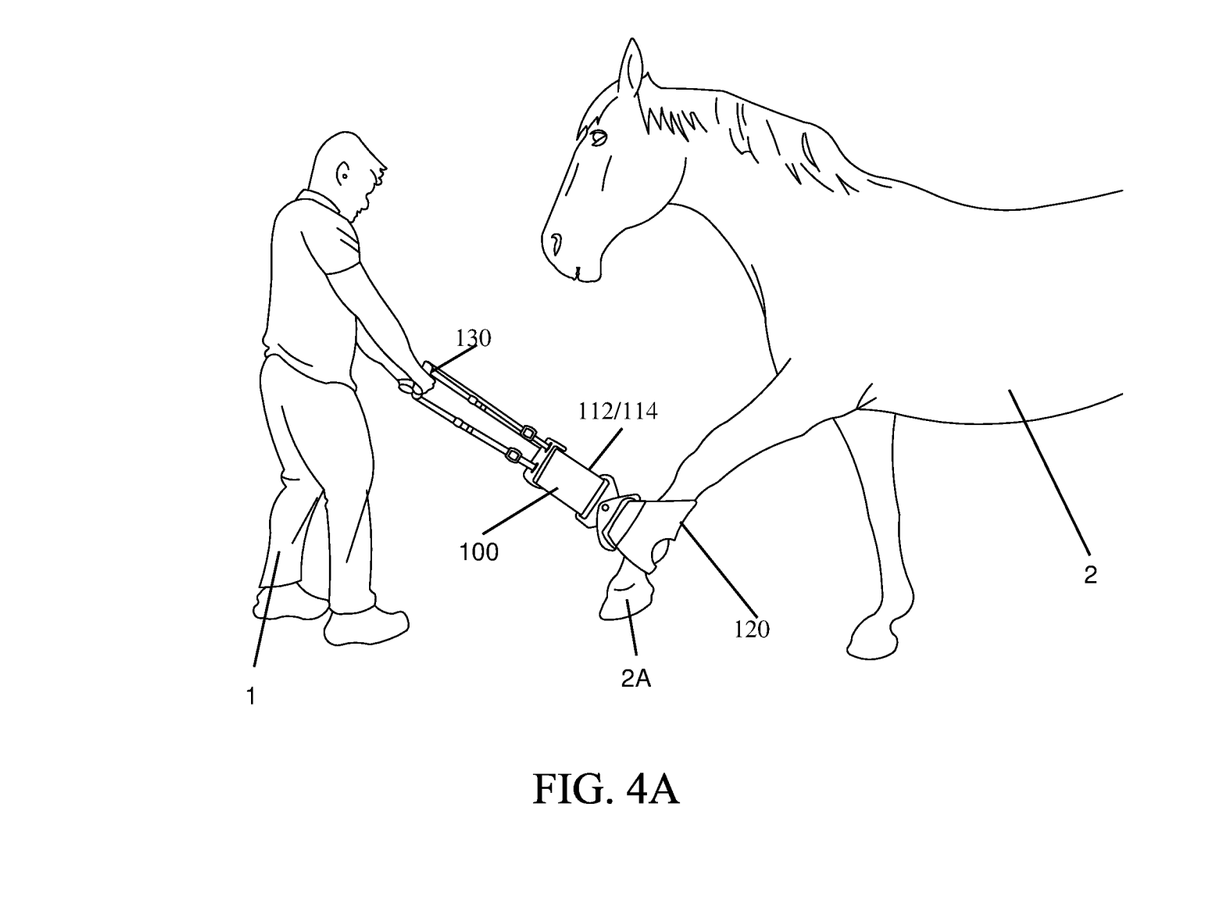
FIG. 4A is a side elevational view of a stretching device being used to stretch a horse in a first manner in accordance with embodiments of the present invention.
Figure 4B:
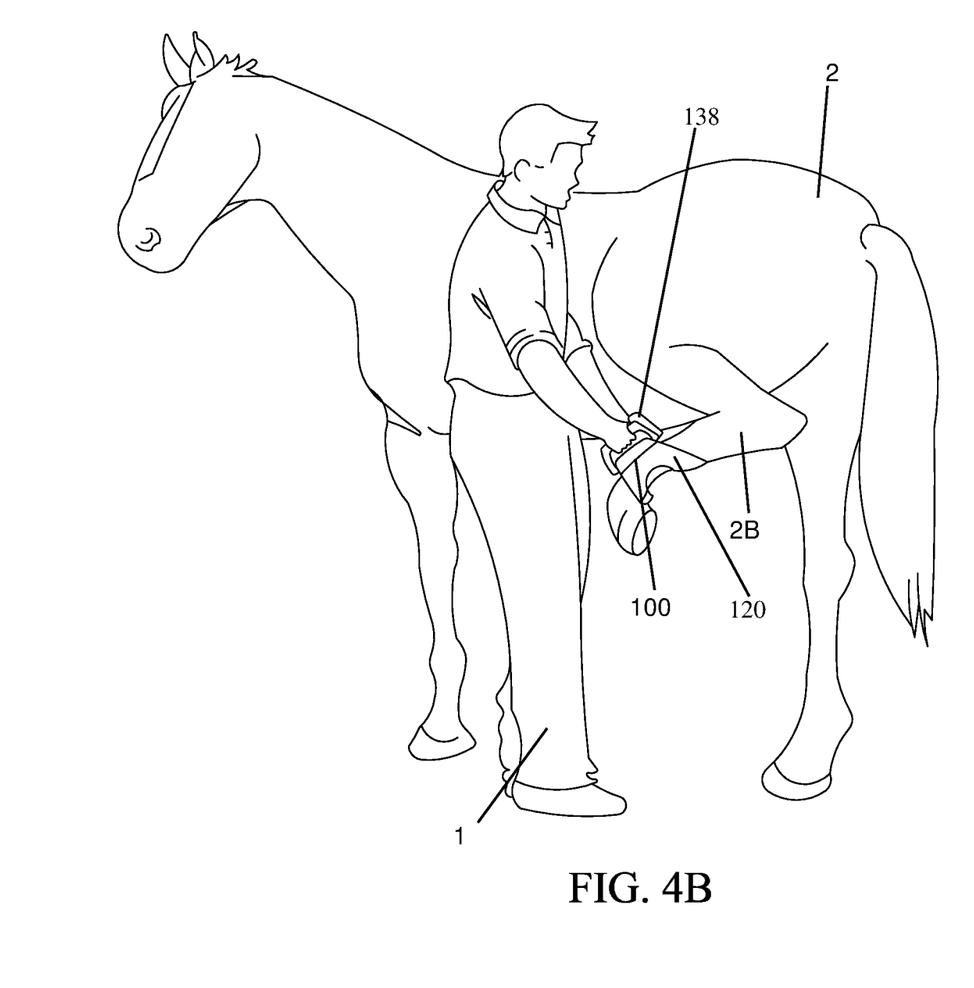
FIG. 4B is a side elevational view of a stretching device being used to stretch a horse in a second manner in accordance with embodiments of the present invention.

FIGS. 4A and 4B illustrate the stretching device 100 being used by a user 1 to stretch a subject 2. The subject 2 in the illustrated embodiment is a horse. It is understood that the stretching device 100 is usable to stretch other subjects, including humans as well as other animals.

In FIG. 4A, the stretching device 100 is in an extended state with the handles 130 and the band sections 112/114 attached. The boot 120 is resting against the rear side of a front limb 2A of the subject 2 near the ankle. The length of the stretching device 100 allows the users to apply a stretching force to the limb 2A while standing upright, reducing the risk of back or other injury to the user 1. The sensors of the stretching device 100 measure any or all of the forward force applied to the limb 2A, the extent of movement, and the orientation of the limb 2A during stretching.

FIG. 4B illustrates the stretching device 100 in a shortened state with the handles 130 and the band sections 112/114 removed. The user 1 is gripping the device 100 by the additional handles 138. The boot 120 is resting against the rear side of a hind limb 2B of the subject 2 near the ankle. As shown, the back limb 2B of the subject 2 has a greater range of forward motion than the front limb 2A. Accordingly, the user 1 can apply the stretching force to the hind limb 2B in a more upright position with the shortened stretching device 100. Shortening the stretching device 100 for stretching the rear limb 2B enables the user 1 to apply the force in a more upward direction, roughly perpendicular to the ankle of the subject 2, and allows the user 1 to stay closer to the subject 2. As in the previous stretch, the sensors in the stretching device 100 measure the force applied to the limb 2B as well as the movement and orientation of the limb 2B during stretching.

These two exemplary stretches are used to illustrate the length adjustment of the stretching device 100. It is understood that many additional stretches can be performed using the stretching device, including stretching other body parts, such as the neck.

In addition to stretching different body parts, the stretching devices 100/300 are usable for multiple methods of equine (or human or other animal) care. For example, the stretching devices 100/300 are usable to diagnose soft tissue injuries. The data measured during the stretching is compared to stored data relating to the same subject and/or stored data relating to similar subjects. Differences between the measured data and the stored data are used to indicate potential soft tissue or other injuries or level of conditioning or athletic ability.

The stretching devices 100/300 are further used to rehabilitate a subject after injury. The stretching device 100/300 is used to stretch the injured body part of the subject. Stretching provides numerous health benefits, such as strengthening muscles and providing blood flow to tendons. The measured sensor data is used to track progress during the rehabilitation process so that the rehabilitation plan can be tailored for optimum benefit to the subject.

In addition, the description of devices described herein are understood to enable one to carry out methods relating to the devices. For example, methods of using the device, methods of stretching horses, methods of monitoring the health of subjects, and methods of manufacturing such stretching devices are all considered and disclosed herein.

What is claimed is:

1. A stretching device for stretching a body part of a subject person or animal comprising:
   a boot having a first side and a second side and having a predetermined shape to complement a contour of the body part of the subject person or animal;
   a first handle coupled to the first side of the boot and a second handle coupled to the second side of the boot;
   a first band pivotally attached at a first end to the first handle and attached at a second end to a third handle;
   a second band pivotally attached at a first end to the second handle and attached at a second end to a fourth handle;
   a first fastener attached to the third handle and a second fastener attached to the fourth handle; and
   a first strap removably attached to the first fastener and a second strap removably attached to the second fastener, wherein the first and second fasteners are configured to permit attachment and removal of the first and second straps, respectively.

2. The stretching device of claim 1 further comprising a sensor mounted proximate the first handle and responsive to a force applied to the boot by pulling on the first and second handles, wherein the sensor generates data related to the force applied.

3. The stretching device of claim 2 wherein the sensor is selected from a group comprising a load cell, a strain gauge, a gyroscope, a mercury switch, an accelerometer, and a combination thereof.

4. A stretching device for stretching a body part of a subject person or animal comprising:
   a boot having a first side and a second side and a predetermined shape to complement a contour of the body part of the subject person or animal;
   a first handle coupled to the first side of the boot and a second handle coupled to the second side of the boot;
   a first band attached at a first end to the first handle and attached at a second end to a third handle;
   a second band attached at a first end to the second handle and attached at a second end to a fourth handle;
   a first fastener attached to the third handle and a second fastener attached to the fourth handle; and
   a first strap attached to the first fastener and a second strap attached to the second fastener, wherein the first and second fasteners are configured to permit adjustment of a length of the first and second straps, respectively.

5. The stretching device of claim 4 further comprising a fifth handle attached to the first strap and a sixth handle attached to the second strap.

6. The stretching device of claim 5 wherein the first and second straps and the fifth and sixth handles are detachable.

7. The stretching device of claim 4 wherein the first and second bands comprise an elastic material.

8. The stretching device of claim 4 wherein the first and second straps comprise elastic material.

9. An exercise system comprising the stretching device of claim 4 wherein the boot is detachable from the stretching device, the exercise system further comprising a second boot shaped to conform to another body part, wherein the second boot is attachable to the stretching device when the boot is detached from the stretching device.

\* \* \* \* \*